United States Patent [19]

Sunley

[11] 4,405,604

[45] Sep. 20, 1983

[54] VETERINARIAN SALVE

[76] Inventor: John T. Sunley, R.R. #6, Springfield, Ill. 62707

[21] Appl. No.: 347,051

[22] Filed: Sep. 9, 1982

[51] Int. Cl.³ .............................................. A61K 33/04
[52] U.S. Cl. ..................................... 424/165; 424/162
[58] Field of Search ........................ 424/162, 164, 165

[56] References Cited

U.S. PATENT DOCUMENTS

| 916,519 | 3/1909 | Wyland | 424/162 |
|---|---|---|---|
| 1,566,271 | 12/1925 | Cesa | 424/162 |

OTHER PUBLICATIONS

Rossoff—Handbook of Veterinary Drugs (1974) Springer Pub. Co. N.Y., N.Y. pp. 87, 144, 298, 303, 435, 436, 580 and 581.

*Primary Examiner*—Sam Rosen
*Attorney, Agent, or Firm*—Ralph F. Staubly

[57] ABSTRACT

A veterinarian salve has an oil base (lard, petrolatum, castor oil), kerosene and flowers of sulfur, and it has sufficient creolin to tastewise discourage dogs from licking-off an application of the salve. The salve is especially effective for treating cuts and open sores in dogs and horses, but is not recommended for cats.

5 Claims, No Drawings

VETERINARIAN SALVE

BACKGROUND AND OBJECT OF THE INVENTION

It is known to make veterinarian salves by combining oils, kerosene and flowers of sulfur, among other medicaments, for application to the open cuts and/or sores of animals (e.g. the patent to Banks, U.S. Pat. No. 377,979, Feb. 4, 1888). But it is not known to combine lard, petroleum jelly, castor oil, sulfur, kerosene and creolin in critical proportions to produce a salve of special effectiveness for treating animals, especially dogs and horses. It is the object of this invention to provide such a salve.

DETAILED DESCRIPTION

The following proportions of ingredients have been found to be particularly effective:
- 1 pound of lard
- 1 pound of petroleum jelly
- ½ pint of castor oil
- 1 pint of kerosene
- 2 pounds of flowers of sulfur
- 2 ounces of creolin

PREPARATION

The lard, petroleum jelly and castor oil are mixed (but not stirred) in a two-gallon kettle, and are heated therein until boiling begins. Then the mixture is allowed to cool to lukewarm and the kerosene is added. Next the four ingredients are heated, boiled for approximately one minute, and again allowed to cool to lukewarm. Then sulfur is added slowly, using a mixer, until an almost running consistency is obtained. Finally the creolin (comprising approximately three percent of the salve by weight) is added and thoroughly mixed-in to produce about four pounds of salve.

TYPICAL TREATMENT USES

For treating sores, mange or kennel sores in dogs, the salve is rubbed onto the affected area thoroughly. For mange a single application is usually sufficient, and normal hair-growth usually follows treatment.

For any open sores or chain-rub injuries on horses, the salve is thoroughly rubbed into the effected area. Normal same-color hair regrowth usually follows cure of the ailment. If scar tissue remains, it can be removed or reduced by washing with common lye soap in warm water, with at least three nightly treatments followed by natural drying (that is, without cloth drying). Usual sanitary conditions are always to be maintained. The principal use of the creolin is to discourage the licking-off of the salve by dogs. The use of the salve on cats is not recommended.

The invention having been described, what is claimed is:

1. A veterinarian salve, comprising a mixture of an oil base as the principal ingredient, flowers of sulfur, and sufficient creolin to tastewise discourage dogs from licking-off an application of said salve to a treatment area.

2. A salve according to claim 1 wherein said oil base comprises ingredients selected from the group consisting of lard, petrolatum and castor oil.

3. A salve according to claim 2 and additionally comprising kerosene.

4. A salve according to claim 3 wherein said creolin comprises approximately three percent of the salve by weight.

5. A salve according to claim 1 wherein said creolin comprises approximately three percent of the salve by weight.

* * * * *